US006919196B1

(12) United States Patent
Nüesch et al.

(10) Patent No.: US 6,919,196 B1
(45) Date of Patent: Jul. 19, 2005

(54) PARVOVIRUS NS1 VARIANTS

(75) Inventors: Jürg Nüesch, Muttenz (CH); Jean Rommelaere, Heidelberg (DE)

(73) Assignee: Deutsches Krabsforschungzentrum Stiftung Des Offentlichen Rechts, Heidelburg (DE)

( * ) Notice: Subject to any disclaimer, the term of this patent is extended or adjusted under 35 U.S.C. 154(b) by 230 days.

(21) Appl. No.: 10/069,056

(22) PCT Filed: Aug. 11, 2000

(86) PCT No.: PCT/EP00/07835

§ 371 (c)(1),
(2), (4) Date: Jul. 29, 2002

(87) PCT Pub. No.: WO01/12666

PCT Pub. Date: Feb. 22, 2001

(30) Foreign Application Priority Data

Aug. 13, 1999 (EP) .......................................... 99115161

(51) Int. Cl.[7] .......................... C12N 7/01; C12N 15/35; C12N 5/10; C12Q 1/70

(52) U.S. Cl. ................................ 435/235.1; 435/320.1; 435/325; 435/69.1; 435/69.3; 435/5; 536/23.72

(58) Field of Search .............................. 435/235.1, 236, 435/320.1, 69.1, 69.3, 325, 252.3, 5; 536/23.72; 514/44, 2; 530/389.4, 388.3

(56) References Cited

PUBLICATIONS

Nuesch et al (Journal of Virology 72:8002–8012, Oct. 1998).*

Nuesch et al (Journal of Virology 72:9966–9977, Dec. 1998).*

Legender et al (Journal of Virology 66:5705–5713, 1992).*

Yeung et al (Virology 181:35–45, 1991).*

Moffatt et al (Journal of Virology 72:3018–3028, Apr. 1998).*

XP–000867510. Legendre et al. "Terminal Regions of the NS–1 Protein of the parvovirus Minute Virus of Mice Are Involved in Cytotoxicity and Promoter trans inhibition." Jour. Of Virol. Oct. 1992. p. 5705–5713.

XP–000867496. Li et al. "Mutation of Lysin 405 to Serine in the Parvovirus H–1 NS1 Abolishes Its Functions for Viral DNA Replication Late Promoter trans Activation, and Cytotoxicity." Jour. Of Vir. Oct. 1990. p. 4654–4660.

XP–002088311. Nuesch et al. "Sequence Motifs in the Replicator Protein of Parvovirus MVM Essential for Nicking and Vocalent Attachment to the Viral Origin: Identification of the Linking Tyrosine." Nuesch et al. Virol. 209, 122–135 (1995).

XP–002088309. Cotmore et al. "The NS1 Polypeptide of the Murine Parvovirus Minute Virus of Mice Binds to DNA Sequences Containing the Motif $[ACCA]_{2-3}$." Jour of Virol. Mar. 1995, p. 1652–1660.

* cited by examiner

*Primary Examiner*—Mary E. Mosher
(74) *Attorney, Agent, or Firm*—Marianne Fuierer; Steven J. Hultquist; Tristan Anne Fuierer

(57) ABSTRACT

The present invention relates to a parvovirus NS1 variant having a shifted equilibrium between the DNA replication and transcription activities (a) and the cytotoxicity activity (b). Furthermore, this invention relates to DNAs coding for these parvovirus NS1 variants and methods of producing them. Additionally, this invention concerns antibodies directed against the parvovirus NS1 variants as well as the use of the DNAs and the parvovirus NS1 variants.

11 Claims, 6 Drawing Sheets

Fig. 1

Wild-type NS1

```
    ATGGCTGGAAATGCTTACTCTGATGAAGTTTTGGGAGCAACCAACTGGTTAAAGGAAAAA
261 ---------+---------+---------+---------+---------+---------+ 320
    TACCGACCTTTACGAATGAGACTACTTCAAAACCCTCGTTGGTTGACCAATTTCCTTTTT

    M  A  G  N  A  Y  S  D  E  V  L  G  A  T  N  W  L  K  E  K  -

    AGTAACCAGGAAGTGTTCTCATTTGTTTTTAAAAATGAAAATGTTCAACTGAATGGAAAA
321 ---------+---------+---------+---------+---------+---------+ 380
    TCATTGGTCCTTCACAAGAGTAAACAAAAATTTTTACTTTTACAAGTTGACTTACCTTTT

    S  N  Q  E  V  F  S  F  V  F  K  N  E  N  V  Q  L  N  G  K  -

    GATATCGGATGGAATAGTTACAAAAAAGAGCTGCAGGAGGACGAGCTGAAATCTTTACAA
381 ---------+---------+---------+---------+---------+---------+ 440
    CTATAGCCTACCTTATCAATGTTTTTTCTCGACGTCCTCCTGCTCGACTTTAGAAATGTT

    D  I  G  W  N  S  Y  K  K  E  L  Q  E  D  E  L  K  S  L  Q  -

    CGAGGAGCGGAAACTACTTGGGACCAAAGCGAGGACATGGAATGGGAAACCACAGTGGAT
441 ---------+---------+---------+---------+---------+---------+ 500
    GCTCCTCGCCTTTGATGAACCCTGGTTTCGCTCCTGTACCTTACCCTTTGGTGTCACCTA

    R  G  A  E  T  T  W  D  Q  S  E  D  M  E  W  E  T  T  V  D  -

    GAAATGACCAAAAAGCAAGTATTCATTTTTGATTCTTTGGTTAAAAAATGTTTATTTGAA
501 ---------+---------+---------+---------+---------+---------+ 560
    CTTTACTGGTTTTTCGTTCATAAGTAAAAACTAAGAAACCAATTTTTTACAAATAAACTT

    E  M  T  K  K  Q  V  F  I  F  D  S  L  V  K  K  C  L  F  E  -

    GTGCTTAACACAAAGAATATATTTCCTGGTGATGTTAATTGGTTTGTGCAACATGAATGG
561 ---------+---------+---------+---------+---------+---------+ 620
    CACGAATTGTGTTTCTTATATAAAGGACCACTACAATTAACCAAACACGTTGTACTTACC

    V  L  N  T  K  N  I  F  P  G  D  V  N  W  F  V  Q  H  E  W  -

    GGAAAAGACCAAGGCTGGCACTGCCATGTACTAATTGGAGGAAAGGACTTTAGTCAAGCT
621 ---------+---------+---------+---------+---------+---------+ 680
    CCTTTTCTGGTTCCGACCGTGACGGTACATGATTAACCTCCTTTCCTGAAATCAGTTCGA

    G  K  D  Q  G  W  H  C  H  V  L  I  G  G  K  D  F  S  Q  A  -

    CAAGGGAAATGGTGGAGAAGGCAACTAAATGTTTACTGGAGCAGATGGTTGGTAACAGCC
681 ---------+---------+---------+---------+---------+---------+ 740
    GTTCCCTTTACCACCTCTTCCGTTGATTTACAAATGACCTCGTCTACCAACCATTGTCGG

    Q  G  K  W  W  R  R  Q  L  N  V  Y  W  S  R  W  L  V  T  A  -

    TGTAATGTGCAACTAACACCAGCTGAAAGAATTAAACTAAGAGAAATAGCAGAAGACAAT
741 ---------+---------+---------+---------+---------+---------+ 800
```

Fig. 1 (Fortsetzung I)

```
     ACATTACACGTTGATTGTGGTCGACTTTCTTAATTTGATTCTCTTTATCGTCTTCTGTTA

     C  N  V  Q  L  T  P  A  E  R  I  K  L  R  E  I  A  E  D  N   -

     GAGTGGGTTACTCTACTTACTTATAAGCATAAGCAAACCAAAAAAGACTATACCAAGTGT
 801 ---------+---------+---------+---------+---------+---------+ 860
     CTCACCCAATGAGATGAATGAATATTCGTATTCGTTTGGTTTTTTCTGATATGGTTCACA

     E  W  V  T  L  L  T  Y  K  H  K  Q  T  K  K  D  Y  T  K  C   -

     GTTCTTTTTGGAAACATGATTGCTTACTATTTTTTAACTAAAAAGAAAATAAGCACTAGT
 861 ---------+---------+---------+---------+---------+---------+ 920
     CAAGAAAAACCTTTGTACTAACGAATGATAAAAAATTGATTTTTCTTTTATTCGTGATCA

     V  L  F  G  N  M  I  A  Y  Y  F  L  T  K  K  K  I  S  T  S   -

     CCACCAAGAGACGGAGGCTATTTTCTTAGCAGTGACTCTGGCTGGAAAACTAACTTTTTA
 921 ---------+---------+---------+---------+---------+---------+ 980
     GGTGGTTCTCTGCCTCCGATAAAAGAATCGTCACTGAGACCGACCTTTTGATTGAAAAAT

     P  P  R  D  G  G  Y  F  L  S  S  D  S  G  W  K  T  N  F  L   -

     AAAGAAGGCGAGCGCCATCTAGTGAGCAAACTATACACTGATGACATGCGGCCAGAAACG
 981 ---------+---------+---------+---------+---------+---------+ 1040
     TTTCTTCCGCTCGCGGTAGATCACTCGTTTGATATGTGACTACTGTACGCCGGTCTTTGC

     K  E  G  E  R  H  L  V  S  K  L  Y  T  D  D  M  R  P  E  T   -

     GTTGAAACCACAGTAACCACTGCGCAGGAAACTAAGCGCGGCAGAATTCAAACTAAAAAA
1041 ---------+---------+---------+---------+---------+---------+ 1100
     CAACTTTGGTGTCATTGGTGACGCGTCCTTTGATTCGCGCCGTCTTAAGTTTGATTTTTT

     V  E  T  T  V  T  T  A  Q  E  T  K  R  G  R  I  Q  T  K  K   -

     GAAGTTTCTATTAAAACTACACTTAAAGAGCTGGTGCATAAAAGAGTAACCTCACCAGAG
1101 ---------+---------+---------+---------+---------+---------+ 1160
     CTTCAAAGATAATTTTGATGTGAATTTCTCGACCACGTATTTTCTCATTGGAGTGGTCTC

     E  V  S  I  K  T  T  L  K  E  L  V  H  K  R  V  T  S  P  E

     GACTCGATGATGATGCAGCCAGACAGTTACATTGAAATGATGGCTCAACCAGGTGGAGAA
1161 ---------+---------+---------+---------+---------+---------+ 1220
     CTGACCTACTACTACGTCGGTCTGTCAATGTAACTTTACTACCGAGTTGGTCCACCTCTT

     D  W  M  M  M  Q  P  D  S  Y  I  E  M  M  A  Q  P  G  G  E   -

     AACCTGCTGAAAAATACGCTAGAGATTTGTACACTAACTCTAGCCAGAACCAAAACAGCA
1221 ---------+---------+---------+---------+---------+---------+ 1280
     TTGGACGACTTTTTATGCGATCTCTAAACATGTGATTGAGATCGGTCTTGGTTTTGTCGT

     N  L  L  K  N  T  L  E  I  C  T  L  T  L  A  R  T  K  T  A

     TTTGACTTAATTTTAGAAAAAGCTGAAACCAGCAAACTAACCAACTTTTCACTGCCTGAC
1281 ---------+---------+---------+---------+---------+---------+ 1340
     AAACTGAATTAAAATCTTTTTCGACTTTGGTCGTTTGATTGGTTGAAAAGTGACGGACTG

     F  D  L  I  L  E  K  A  E  T  S  K  L  T  N  F  S  L  P  D   -

     ACAAGAACCTGCAGAATTTTTGCTTTTCATGGCTGGAACTATGTTAAAGTTTGCCATGCT
1341 ---------+---------+---------+---------+---------+---------+ 1400
     TGTTCTTGGACGTCTTAAAAACGAAAAGTACCGACCTTGATACAATTTCAAACGGTACGA

     T  R  T  C  R  I  F  A  F  H  G  W  N  Y  V  K  V  C  H  A   -
```

Fig. 1 (Fortsetzung II)

```
     ATTTGCTGTGTTTTAAACAGACAAGGAGGCAAAAGAAATACTGTTTTATTTCATGGACCA
1401 ---------+---------+---------+---------+---------+---------+ 1460
     TAAACGACACAAAATTTGTCTGTTCCTCCGTTTTCTTTATGACAAAATAAAGTACCTGGT

     I  C  C  V  L  N  R  Q  G  G  K  R  N  T  V  L  F  H  G  P  -

     GCCAGCACAGGCAAATCTATTATTGCACAAGCCATAGCACAAGCAGTTGGCAATGTTGGT
1461 ---------+---------+---------+---------+---------+---------+ 1520
     CGGTCGTGTCCGTTTAGATAATAACGTGTTCGGTATCGTGTTCGTCAACCGTTACAACCA

     A  S  T  G  K  S  I  I  A  Q  A  I  A  Q  A  V  G  N  V  G  -

     TGCTATAATGCAGCCAATGTAAACTTTCCATTTAATGACTGTACCAACAAGAACTTGATT
1521 ---------+---------+---------+---------+---------+---------+ 1580
     ACGATATTACGTCGGTTACATTTGAAAGGTAAATTACTGACATGGTTGTTCTTGAACTAA

     C  Y  N  A  A  N  V  N  F  P  F  N  D  C  T  N  K  N  L  I  -

     TGGGTAGAAGAAGCTGGTAACTTTGGACAGCAAGTAAACCAGTTTAAAGCCATTTGCTCT
1581 ---------+---------+---------+---------+---------+---------+ 1640
     ACCCATCTTCTTCGACCATTGAAACCTGTCGTTCATTTGGTCAAATTTCGGTAAACGAGA

     W  V  E  E  A  G  N  F  G  Q  Q  V  N  Q  F  K  A  I  C  S  -

     GGTCAAACTATTCGCATTGATCAAAAAGGAAAAGGCAGCAAACAGATTGAACCAACACCA
1641 ---------+---------+---------+---------+---------+---------+ 1700
     CCAGTTTGATAAGCGTAACTAGTTTTTCCTTTTCCGTCGTTTGTCTAACTTGGTTGTGGT

     G  Q  T  I  R  I  D  Q  K  G  K  G  S  K  Q  I  E  P  T  P  -

     GTCATCATGACCACAAATGAGAACATTACAGTGGTCAGAATAGGCTGCGAAGAAAGACCA
1701 ---------+---------+---------+---------+---------+---------+ 1760
     CAGTAGTACTGGTGTTTACTCTTGTAATGTCACCAGTCTTATCCGACGCTTCTTTCTGGT

     V  I  M  T  T  N  E  N  I  T  V  V  R  I  G  C  E  E  R  P  -

     GAACACACTCAACCAATCAGAGACAGAATGCTTAACATTCATCTAACACATACCTTGCCT
1761 ---------+---------+---------+---------+---------+---------+ 1820
     CTTGTGTGAGTTGGTTAGTCTCTGTCTTACGAATTGTAAGTAGATTGTGTATGGAACGGA

     E  H  T  Q  P  I  R  D  R  M  L  N  I  H  L  T  H  T  L  P  -

     GGTGACTTTGGTTTGGTTGACAAAAATGAATGGCCCATGATTTGTGCTTGGTTGGTAAAG
1821 ---------+---------+---------+---------+---------+---------+ 1880
     CCACTGAAACCAAACCAACTGTTTTTACTTACCGGGTACTAAACACGAACCAACCATTTC

     G  D  F  G  L  V  D  K  N  E  W  P  M  I  C  A  W  L  V  K  -

     AATGGTTACCAATCTACCATGGCAAGCTACTGTGCTAAATGGGGCAAAGTTCCTGATTGG
1881 ---------+---------+---------+---------+---------+---------+ 1940
     TTACCAATGGTTAGATGGTACCGTTCGATGACACGATTTACCCCGTTTCAAGGACTAACC

     N  G  Y  Q  S  T  M  A  S  Y  C  A  K  W  G  K  V  P  D  W  -

     TCAGAAAACTGGGCGGAGCCAAAGGTGCCAACTCCTATAAATTTACTAGGTTCGGCACGC
1941 ---------+---------+---------+---------+---------+---------+ 2000
     AGTCTTTTGACCCGCCTCGGTTTCCACGGTTGAGGATATTTAAATGATCCAAGCCGTGCG

     S  E  N  W  A  E  P  K  V  P  T  P  I  N  L  L  G  S  A  R  -

     TCACCATTCACGACACCGAAAAGTACGCCTCTCAGCCAGAACTATGCACTAACTCCACTT
2001 ---------+---------+---------+---------+---------+---------+ 2060
     AGTGGTAAGTGCTGTGGCTTTTCATGCGGAGAGTCGGTCTTGATACGTGATTGAGGTGAA
```

Fig. 1 (Fortsetzung III)

```
     S   P   F   T   T   P   K   S   T   P   L   S   Q   N   Y   A   L   T   P   L   -

     GCATCGGATCTCGAGGACCTGGCTTTAGAGCCTTGGAGCACACCAAATACTCCTGTTGCG
2061 ---------+---------+---------+---------+---------+---------+ 2120
     CGTAGCCTAGAGCTCCTGGACCGAAATCTCGGAACCTCGTGTGGTTTATGAGGACAACGC

     A   S   D   L   E   D   L   A   L   E   P   W   S   T   P   N   T   P   V   A   -

     GGCACTGCAGAAACCCAGAACACTGGGGAAGCTGGTTCCAAAGCCTGCCAAGATGGTCAA
2121 ---------+---------+---------+---------+---------+---------+ 2180
     CCGTGACGTCTTTGGGTCTTGTGACCCCTTCGACCAAGGTTTCGGACGGTTCTACCAGTT

     G   T   A   E   T   Q   N   T   G   E   A   G   S   K   A   C   Q   D   G   Q   -

     CTGAGCCCAACTTGGTCAGAGATCGAGGAGGATTTGAGAGCGTGCTTCGGTGCGGAACCG
2181 ---------+---------+---------+---------+---------+---------+ 2240
     GACTCGGGTTGAACCAGTCTCTAGCTCCTCCTAAACTCTCGCACGAAGCCACGCCTTGGC

     L   S   P   T   W   S   E   I   E   E   D   L   R   A   C   F   G   A   E   P   -

     TTGAAGAAAGACTTCAGCGAGCCGCTGAACTTGGACTAA
2241 ---------+---------+---------+--------- 2279
     AACTTCTTTCTGAAGTCGCTCGGCGACTTGAACCTGATT

     L   K   K   D   F   S   E   P   L   N   L   D   *   -
```

1100 - 261 Wildtype-NS1-Sequence

```
            →G
     GAAGTTTCTATTAAAACTACACTTAAAGAGCTGGTGCATAAAAGAGTAACCTCACCAGAG
1101 ---------+---------+---------+---------+---------+---------+ 1160
     CTTCAAAGATAATTTTGATGTGAATTTCTCGACCACGTATTTTCTCATTGGAGTGGTCTC

     E  V [S] I  K  T  T  L  K  E  L  V  H  K  R  V  T  S  P  E  -
         →A  S283A
```

1161 - 2279 Wildtype-NS1-Sequence

Fig. 1.2

1340 - 261 Wildtype-NS1-Sequence

```
             →G
     ACAAGAACCTGCAGAATTTTTGCTTTTCATGGCTGGAACTATGTTAAAGTTTGCCATGCT
1341 ---------+---------+---------+---------+---------+---------+ 1400
     TGTTCTTGGACGTCTTAAAAACGAAAAGTACCGACCTTGATACAATTTCAAACGGTACGA

     T  R [T] C  R  I  F  A  F  H  G  W  N  Y  V  K  V  C  H  A  -
         →A  T363A
```

1400 - 261  Wildtype-NS1-Sequence

```
                                            →G
       ATTTGCTGTGTTTTAAACAGACAAGGAGGCAAAAGAAATACTGTTTTATTTCATGGACCA
1401   ------------+---------+---------+--------++---------+---------+ 1460
       TAAACGACACAAAATTTGTCTGTTCCTCCGTTTTCTTTATGACAAAATAAAGTACCTGGT

        I  C  C  V  L  N  R  Q  G  G  K  R  N  T  V  L  F  H  G  P  -
                                                →A  T394A
```

1461 - 2279  Wildtype-NS1-Sequence

Fig. 1.4

1640 - 261  Wildtype-NS1-Sequence

```
             →G
       GGTCAAACTATTCGCATTGATCAAAAAGGAAAAGGCAGCAAACAGATTGAACCAACACCA
1641   -----++---+---------+---------+---------+---------+---------+ 1700
       CCAGTTTGATAAGCGTAACTAGTTTTTCCTTTTCCGTCGTTTGTCTAACTTGGTTGTGGT

        G  Q  T  I  R  I  D  Q  K  G  K  G  S  K  Q  I  E  P  T  P  -
           →A  T463A
```

1701 - 2279  Wildtype-NS1-Sequence

SEQUENCE LISTING

```
<160> NUMBER OF SEQ ID NOS: 18

<210> SEQ ID NO 1
<211> LENGTH: 2019
<212> TYPE: DNA
<213> ORGANISM: Wildtype Parvovirus NS1

<400> SEQUENCE: 1
```

-continued

```
atggctggaa atgcttactc tgatgaagtt ttgggagcaa ccaactggtt aaaggaaaaa     60

agtaaccagg aagtgttctc atttgttttt aaaaatgaaa atgttcaact gaatggaaaa    120

gatatcggat ggaatagtta caaaaaagag ctgcaggagg acgagctgaa atctttacaa    180

cgaggagcgg aaactacttg ggaccaaagc gaggacatgg aatgggaaac cacagtggat    240

gaaatgacca aaaagcaagt attcattttt gattctttgg ttaaaaaatg tttatttgaa    300

gtgcttaaca caaagaatat atttcctggt gatgttaatt ggtttgtgca acatgaatgg    360

ggaaaagacc aaggctggca ctgccatgta ctaattggag gaaaggactt tagtcaagct    420

caagggaaat ggtggagaag gcaactaaat gtttactgga gcagatggtt ggtaacagcc    480

tgtaatgtgc aactaacacc agctgaaaga attaaactaa gagaaatagc agaagacaat    540

gagtgggtta ctctacttac ttataagcat aagcaaacca aaaaagacta taccaagtgt    600

gttctttttg gaaacatgat tgcttactat tttttaacta aaaagaaaat aagcactagt    660

ccaccaagag acggaggcta ttttcttagc agtgactctg gctggaaaac taacttttta    720

aaagaaggcg agcgccatct agtgagcaaa ctatacactg atgacatgcg gccagaaacg    780

gttgaaacca cagtaaccac tgcgcaggaa actaagcgcg gcagaattca aactaaaaaa    840

gaagtttcta ttaaaactac acttaaagag ctggtgcata aaagagtaac ctcaccagag    900

gactggatga tgatgcagcc agacagttac attgaaatga tggctcaacc aggtggagaa    960

aacctgctga aaaatacgct agagatttgt acactaactc tagccagaac caaaacagca   1020

tttgacttaa ttttagaaaa agctgaaacc agcaaactaa ccaacttttc actgcctgac   1080

acaagaacct gcagaatttt tgcttttcat ggctggaact atgttaaagt ttgccatgct   1140

atttgctgtg ttttaaacag acaaggaggc aaaagaaata ctgtttttatt tcatggacca  1200

gccagcacag gcaaatctat tattgcacaa gccatagcac aagcagttgg caatgttggt   1260

tgctataatg cagccaatgt aaactttcca tttaatgact gtaccaacaa gaacttgatt   1320

tgggtagaag aagctggtaa ctttggacag caagtaaacc agtttaaagc catttgctct   1380

ggtcaaacta ttcgcattga tcaaaaagga aaaggcagca aacagattga accaacacca   1440

gtcatcatga ccacaaatga gaacattaca gtggtcagaa taggctgcga agaaagacca   1500

gaacacactc aaccaatcag agacagaatg cttaacattc atctaacaca taccttgcct   1560

ggtgactttg gtttggttga caaaaatgaa tggcccatga tttgtgcttg gttggtaaag   1620

aatggttacc aatctaccat ggcaagctac tgtgctaaat ggggcaaagt tcctgattgg   1680

tcagaaaact gggcggagcc aaaggtgcca actcctataa atttactagg ttcggcacgc   1740

tcaccattca cgacaccgaa aagtacgcct ctcagccaga actatgcact aactccactt   1800

gcatcggatc tcgaggacct ggctttagag ccttggagca caccaaatac tcctgttgcg   1860

ggcactgcag aaacccagaa cactggggaa gctggttcca aagcctgcca agatggtcaa   1920

ctgagcccaa cttggtcaga gatcgaggag gatttgagag cgtgcttcgg tgcggaaccg   1980

ttgaagaaag acttcagcga gccgctgaac ttggactaa                           2019
```

<210> SEQ ID NO 2
<211> LENGTH: 672
<212> TYPE: PRT
<213> ORGANISM: Wildtype Parvovirus NS1

<400> SEQUENCE: 2

```
Met Ala Gly Asn Ala Tyr Ser Asp Glu Val Leu Gly Ala Thr Asn Trp
1               5                   10                  15
```

-continued

```
Leu Lys Glu Lys Ser Asn Gln Glu Val Phe Ser Phe Val Phe Lys Asn
            20                  25                  30

Glu Asn Val Gln Leu Asn Gly Lys Asp Ile Gly Trp Asn Ser Tyr Lys
        35                  40                  45

Lys Glu Leu Gln Glu Asp Glu Leu Lys Ser Leu Gln Arg Gly Ala Glu
    50                  55                  60

Thr Thr Trp Asp Gln Ser Glu Asp Met Glu Trp Glu Thr Thr Val Asp
65                  70                  75                  80

Glu Met Thr Lys Lys Gln Val Phe Ile Phe Asp Ser Leu Val Lys Lys
                85                  90                  95

Cys Leu Phe Glu Val Leu Asn Thr Lys Asn Ile Phe Pro Gly Asp Val
            100                 105                 110

Asn Trp Phe Val Gln His Glu Trp Gly Lys Asp Gln Gly Trp His Cys
        115                 120                 125

His Val Leu Ile Gly Gly Lys Asp Phe Ser Gln Ala Gln Gly Lys Trp
    130                 135                 140

Trp Arg Arg Gln Leu Asn Val Tyr Trp Ser Arg Trp Leu Val Thr Ala
145                 150                 155                 160

Cys Asn Val Gln Leu Thr Pro Ala Glu Arg Ile Lys Leu Arg Glu Ile
                165                 170                 175

Ala Glu Asp Asn Glu Trp Val Thr Leu Leu Thr Tyr Lys His Lys Gln
            180                 185                 190

Thr Lys Lys Asp Tyr Thr Lys Cys Val Leu Phe Gly Asn Met Ile Ala
        195                 200                 205

Tyr Tyr Phe Leu Thr Lys Lys Lys Ile Ser Thr Ser Pro Pro Arg Asp
    210                 215                 220

Gly Gly Tyr Phe Leu Ser Ser Asp Ser Gly Trp Lys Thr Asn Phe Leu
225                 230                 235                 240

Lys Glu Gly Glu Arg His Leu Val Ser Lys Leu Tyr Thr Asp Asp Met
                245                 250                 255

Arg Pro Glu Thr Val Glu Thr Thr Val Thr Thr Ala Gln Glu Thr Lys
            260                 265                 270

Arg Gly Arg Ile Gln Thr Lys Lys Glu Val Ser Ile Lys Thr Thr Leu
        275                 280                 285

Lys Glu Leu Val His Lys Arg Val Thr Ser Pro Glu Asp Trp Met Met
    290                 295                 300

Met Gln Pro Asp Ser Tyr Ile Glu Met Met Ala Gln Pro Gly Gly Glu
305                 310                 315                 320

Asn Leu Leu Lys Asn Thr Leu Glu Ile Cys Thr Leu Thr Leu Ala Arg
                325                 330                 335

Thr Lys Thr Ala Phe Asp Leu Ile Leu Glu Lys Ala Glu Thr Ser Lys
            340                 345                 350

Leu Thr Asn Phe Ser Leu Pro Asp Thr Arg Thr Cys Arg Ile Phe Ala
        355                 360                 365

Phe His Gly Trp Asn Tyr Val Lys Val Cys His Ala Ile Cys Cys Val
    370                 375                 380

Leu Asn Arg Gln Gly Gly Lys Arg Asn Thr Val Leu Phe His Gly Pro
385                 390                 395                 400

Ala Ser Thr Gly Lys Ser Ile Ile Ala Gln Ala Ile Ala Gln Ala Val
                405                 410                 415

Gly Asn Val Gly Cys Tyr Asn Ala Ala Asn Val Asn Phe Pro Phe Asn
            420                 425                 430

Asp Cys Thr Asn Lys Asn Leu Ile Trp Val Glu Glu Ala Gly Asn Phe
```

-continued

```
        435                 440                 445

Gly Gln Gln Val Asn Gln Phe Lys Ala Ile Cys Ser Gly Gln Thr Ile
    450                 455                 460

Arg Ile Asp Gln Lys Gly Lys Gly Ser Lys Gln Ile Glu Pro Thr Pro
465                 470                 475                 480

Val Ile Met Thr Thr Asn Glu Asn Ile Thr Val Val Arg Ile Gly Cys
                485                 490                 495

Glu Glu Arg Pro Glu His Thr Gln Pro Ile Arg Asp Arg Met Leu Asn
            500                 505                 510

Ile His Leu Thr His His Leu Pro Gly Asp Phe Gly Leu Val Asp Lys
        515                 520                 525

Asn Glu Trp Pro Met Ile Cys Ala Trp Leu Val Lys Asn Gly Tyr Gln
    530                 535                 540

Ser Thr Met Ala Ser Tyr Cys Ala Lys Trp Gly Lys Val Pro Asp Trp
545                 550                 555                 560

Ser Glu Asn Trp Ala Glu Pro Lys Val Pro Thr Pro Ile Asn Leu Leu
                565                 570                 575

Gly Ser Ala Arg Ser Pro Phe Thr Thr Pro Lys Ser Thr Pro Leu Ser
            580                 585                 590

Gln Asn Tyr Ala Leu Thr Pro Leu Ala Ser Asp Leu Glu Asp Leu Ala
        595                 600                 605

Leu Glu Pro Trp Ser Thr Pro Asn Thr Pro Val Ala Gly Thr Ala Glu
    610                 615                 620

Thr Gln Asn Thr Gly Glu Ala Gly Ser Lys Ala Cys Gln Asp Gly Gln
625                 630                 635                 640

Leu Ser Pro Thr Trp Ser Glu Ile Glu Glu Asp Leu Arg Ala Cys Phe
                645                 650                 655

Gly Ala Glu Pro Leu Lys Lys Asp Phe Ser Glu Pro Leu Asn Leu Asp
            660                 665                 670


<210> SEQ ID NO 3
<211> LENGTH: 60
<212> TYPE: DNA
<213> ORGANISM: Part of Parvovirus NS1 Variant

<400> SEQUENCE: 3

gaagttgcta ttaaaactac acttaaagag ctggtgcata aaagagtaac ctcaccagag     60


<210> SEQ ID NO 4
<211> LENGTH: 2019
<212> TYPE: DNA
<213> ORGANISM: Parvovirus NS1 Variant

<400> SEQUENCE: 4

atggctggaa atgcttactc tgatgaagtt ttgggagcaa ccaactggtt aaaggaaaaa     60

agtaaccagg aagtgttctc atttgttttt aaaaatgaaa atgttcaact gaatggaaaa    120

gatatcggat ggaatagtta caaaaaagag ctgcaggagg acgagctgaa atctttacaa    180

cgaggagcgg aaactacttg ggaccaaagc gaggacatgg aatgggaaac cacagtggat    240

gaaatgacca aaaagcaagt attcattttt gattctttgg ttaaaaaatg tttatttgaa    300

gtgcttaaca caaagaatat atttcctggt gatgttaatt ggtttgtgca acatgaatgg    360

ggaaaagacc aaggctggca ctgccatgta ctaattggag gaaaggactt tagtcaagct    420

caagggaaat ggtggagaag gcaactaaat gtttactgga gcagatggtt ggtaacagcc    480

tgtaatgtgc aactaacacc agctgaaaga attaaactaa gagaaatagc agaagacaat    540
```

-continued

```
gagtgggtta ctctacttac ttataagcat aagcaaacca aaaaagacta taccaagtgt    600

gttctttttg gaaacatgat tgcttactat tttttaacta aaaagaaaat aagcactagt    660

ccaccaagag acggaggcta ttttcttagc agtgactctg gctggaaaac taactttttta    720

aaagaaggcg agcgccatct agtgagcaaa ctatacactg atgacatgcg gccagaaacg    780

gttgaaacca cagtaaccac tgcgcaggaa actaagcgcg gcagaattca aactaaaaaa    840

gaagttgcta ttaaaactac acttaaagag ctggtgcata aaagagtaac ctcaccagag    900

gactggatga tgatgcagcc agacagttac attgaaatga tggctcaacc aggtggagaa    960

aacctgctga aaaatacgct agagatttgt acactaactc tagccagaac caaaacagca   1020

tttgacttaa ttttagaaaa agctgaaacc agcaaactaa ccaacttttc actgcctgac   1080

acaagaacct gcagaatttt tgcttttcat ggctggaact atgttaaagt ttgccatgct   1140

atttgctgtg ttttaaacag acaaggaggc aaaagaaata ctgttttatt tcatggacca   1200

gccagcacag gcaaatctat tattgcacaa gccatagcac aagcagttgg caatgttggt   1260

tgctataatg cagccaatgt aaactttcca tttaatgact gtaccaacaa gaacttgatt   1320

tgggtagaag aagctggtaa ctttggacag caagtaaacc agtttaaagc catttgctct   1380

ggtcaaacta ttcgcattga tcaaaaagga aaaggcagca aacagattga accaacacca   1440

gtcatcatga ccacaaatga gaacattaca gtggtcagaa taggctgcga agaaagacca   1500

gaacacactc aaccaatcag agacagaatg cttaacattc atctaacaca taccttgcct   1560

ggtgactttg gtttggttga caaaaatgaa tggcccatga tttgtgcttg gttggtaaag   1620

aatggttacc aatctaccat ggcaagctac tgtgctaaat ggggcaaagt tcctgattgg   1680

tcagaaaact gggcggagcc aaaggtgcca actcctataa atttactagg ttcggcacgc   1740

tcaccattca cgacaccgaa aagtacgcct ctcagccaga actatgcact aactccactt   1800

gcatcggatc tcgaggacct ggctttagag ccttggagca caccaaatac tcctgttgcg   1860

ggcactgcag aaacccagaa cactggggaa gctggttcca aagcctgcca agatggtcaa   1920

ctgagcccaa cttggtcaga gatcgaggag gatttgagag cgtgcttcgg tgcggaaccg   1980

ttgaagaaag acttcagcga gccgctgaac ttggactaa                         2019
```

```
<210> SEQ ID NO 5
<211> LENGTH: 20
<212> TYPE: PRT
<213> ORGANISM: Part of Parvovirus NS1 Variant

<400> SEQUENCE: 5

Glu Val Ala Ile Lys Thr Thr Leu Lys Glu Leu Val His Lys Arg Val
1               5                   10                  15

Thr Ser Pro Glu
            20


<210> SEQ ID NO 6
<211> LENGTH: 672
<212> TYPE: PRT
<213> ORGANISM: Parvovirus NS1 Variant

<400> SEQUENCE: 6

Met Ala Gly Asn Ala Tyr Ser Asp Glu Val Leu Gly Ala Thr Asn Trp
1               5                   10                  15

Leu Lys Glu Lys Ser Asn Gln Glu Val Phe Ser Phe Val Phe Lys Asn
            20                  25                  30
```

-continued

```
Glu Asn Val Gln Leu Asn Gly Lys Asp Ile Gly Trp Asn Ser Tyr Lys
        35                  40                  45

Lys Glu Leu Gln Glu Asp Glu Leu Lys Ser Leu Gln Arg Gly Ala Glu
    50                  55                  60

Thr Thr Trp Asp Gln Ser Glu Asp Met Glu Trp Glu Thr Thr Val Asp
65                  70                  75                  80

Glu Met Thr Lys Lys Gln Val Phe Ile Phe Asp Ser Leu Val Lys Lys
                85                  90                  95

Cys Leu Phe Glu Val Leu Asn Thr Lys Asn Ile Phe Pro Gly Asp Val
            100                 105                 110

Asn Trp Phe Val Gln His Glu Trp Gly Lys Asp Gln Gly Trp His Cys
        115                 120                 125

His Val Leu Ile Gly Gly Lys Asp Phe Ser Gln Ala Gln Gly Lys Trp
    130                 135                 140

Trp Arg Arg Gln Leu Asn Val Tyr Trp Ser Arg Trp Leu Val Thr Ala
145                 150                 155                 160

Cys Asn Val Gln Leu Thr Pro Ala Glu Arg Ile Lys Leu Arg Glu Ile
                165                 170                 175

Ala Glu Asp Asn Glu Trp Val Thr Leu Leu Thr Tyr Lys His Lys Gln
            180                 185                 190

Thr Lys Lys Asp Tyr Thr Lys Cys Val Leu Phe Gly Asn Met Ile Ala
        195                 200                 205

Tyr Tyr Phe Leu Thr Lys Lys Lys Ile Ser Thr Ser Pro Pro Arg Asp
    210                 215                 220

Gly Gly Tyr Phe Leu Ser Ser Asp Ser Gly Trp Lys Thr Asn Phe Leu
225                 230                 235                 240

Lys Glu Gly Glu Arg His Leu Val Ser Lys Leu Tyr Thr Asp Asp Met
                245                 250                 255

Arg Pro Glu Thr Val Glu Thr Thr Val Thr Thr Ala Gln Glu Thr Lys
            260                 265                 270

Arg Gly Arg Ile Gln Thr Lys Lys Glu Val Ala Ile Lys Thr Thr Leu
        275                 280                 285

Lys Glu Leu Val His Lys Arg Val Thr Ser Pro Glu Asp Trp Met Met
    290                 295                 300

Met Gln Pro Asp Ser Tyr Ile Glu Met Met Ala Gln Pro Gly Gly Glu
305                 310                 315                 320

Asn Leu Leu Lys Asn Thr Leu Glu Ile Cys Thr Leu Thr Leu Ala Arg
                325                 330                 335

Thr Lys Thr Ala Phe Asp Leu Ile Leu Glu Lys Ala Glu Thr Ser Lys
            340                 345                 350

Leu Thr Asn Phe Ser Leu Pro Asp Thr Arg Thr Cys Arg Ile Phe Ala
        355                 360                 365

Phe His Gly Trp Asn Tyr Val Lys Val Cys His Ala Ile Cys Cys Val
    370                 375                 380

Leu Asn Arg Gln Gly Gly Lys Arg Asn Thr Val Leu Phe His Gly Pro
385                 390                 395                 400

Ala Ser Thr Gly Lys Ser Ile Ile Ala Gln Ala Ile Ala Gln Ala Val
                405                 410                 415

Gly Asn Val Gly Cys Tyr Asn Ala Ala Asn Val Asn Phe Pro Phe Asn
            420                 425                 430

Asp Cys Thr Asn Lys Asn Leu Ile Trp Val Glu Glu Ala Gly Asn Phe
        435                 440                 445

Gly Gln Gln Val Asn Gln Phe Lys Ala Ile Cys Ser Gly Gln Thr Ile
```

-continued

```
    450                 455                 460

Arg Ile Asp Gln Lys Gly Lys Gly Ser Lys Gln Ile Glu Pro Thr Pro
465                 470                 475                 480

Val Ile Met Thr Thr Asn Glu Asn Ile Thr Val Val Arg Ile Gly Cys
                485                 490                 495

Glu Glu Arg Pro Glu His Thr Gln Pro Ile Arg Asp Arg Met Leu Asn
            500                 505                 510

Ile His Leu Thr His His Leu Pro Gly Asp Phe Gly Leu Val Asp Lys
        515                 520                 525

Asn Glu Trp Pro Met Ile Cys Ala Trp Leu Val Lys Asn Gly Tyr Gln
    530                 535                 540

Ser Thr Met Ala Ser Tyr Cys Ala Lys Trp Gly Lys Val Pro Asp Trp
545                 550                 555                 560

Ser Glu Asn Trp Ala Glu Pro Lys Val Pro Thr Pro Ile Asn Leu Leu
                565                 570                 575

Gly Ser Ala Arg Ser Pro Phe Thr Thr Pro Lys Ser Thr Pro Leu Ser
            580                 585                 590

Gln Asn Tyr Ala Leu Thr Pro Leu Ala Ser Asp Leu Glu Asp Leu Ala
        595                 600                 605

Leu Glu Pro Trp Ser Thr Pro Asn Thr Pro Val Ala Gly Thr Ala Glu
    610                 615                 620

Thr Gln Asn Thr Gly Glu Ala Gly Ser Lys Ala Cys Gln Asp Gly Gln
625                 630                 635                 640

Leu Ser Pro Thr Trp Ser Glu Ile Glu Glu Asp Leu Arg Ala Cys Phe
                645                 650                 655

Gly Ala Glu Pro Leu Lys Lys Asp Phe Ser Glu Pro Leu Asn Leu Asp
            660                 665                 670


<210> SEQ ID NO 7
<211> LENGTH: 60
<212> TYPE: DNA
<213> ORGANISM: Part of Parvovirus NS1 Variant

<400> SEQUENCE: 7

acaagagcct gcagaatttt tgcttttcat ggctggaact atgttaaagt ttgccatgct     60


<210> SEQ ID NO 8
<211> LENGTH: 2019
<212> TYPE: DNA
<213> ORGANISM: Parvovirus NS1 Variant

<400> SEQUENCE: 8

atggctggaa atgcttactc tgatgaagtt ttgggagcaa ccaactggtt aaaggaaaaa     60

agtaaccagg aagtgttctc atttgttttt aaaaatgaaa atgttcaact gaatggaaaa    120

gatatcggat ggaatagtta caaaaaagag ctgcaggagg acgagctgaa atctttacaa    180

cgaggagcgg aaactacttg ggaccaaagc gaggacatgg aatgggaaac cacagtggat    240

gaaatgacca aaaagcaagt attcattttt gattctttgg ttaaaaaatg tttatttgaa    300

gtgcttaaca caaagaatat atttcctggt gatgttaatt ggtttgtgca acatgaatgg    360

ggaaaagacc aaggctggca ctgccatgta ctaattggag gaaaggactt tagtcaagct    420

caagggaaat ggtggagaag gcaactaaat gtttactgga gcagatggtt ggtaacagcc    480

tgtaatgtgc aactaacacc agctgaaaga attaaactaa gagaaatagc agaagacaat    540

gagtgggtta ctctacttac ttataagcat aagcaaacca aaaaagacta taccaagtgt    600
```

-continued

```
gttctttttg gaaacatgat tgcttactat tttttaacta aaaagaaaat aagcactagt    660

ccaccaagag acggaggcta ttttcttagc agtgactctg gctggaaaac taacttttta    720

aaagaaggcg agcgccatct agtgagcaaa ctatacactg atgacatgcg gccagaaacg    780

gttgaaacca cagtaaccac tgcgcaggaa actaagcgcg gcagaattca aactaaaaaa    840

gaagtttcta ttaaaactac acttaaagag ctggtgcata aaagagtaac ctcaccagag    900

gactggatga tgatgcagcc agacagttac attgaaatga tggctcaacc aggtggagaa    960

aacctgctga aaaatacgct agagatttgt acactaactc tagccagaac caaaacagca   1020

tttgacttaa ttttagaaaa agctgaaacc agcaaactaa ccaacttttc actgcctgac   1080

acaagagcct gcagaatttt tgcttttcat ggctggaact atgttaaagt ttgccatgct   1140

atttgctgtg ttttaaacag acaaggaggc aaaagaaata ctgtttttatt tcatggacca   1200

gccagcacag gcaaatctat tattgcacaa gccatagcac aagcagttgg caatgttggt   1260

tgctataatg cagccaatgt aaactttcca tttaatgact gtaccaacaa gaacttgatt   1320

tgggtagaag aagctggtaa ctttggacag caagtaaacc agtttaaagc catttgctct   1380

ggtcaaacta ttcgcattga tcaaaaagga aaaggcagca aacagattga accaacacca   1440

gtcatcatga ccacaaatga gaacattaca gtggtcagaa taggctgcga agaaagacca   1500

gaacacactc aaccaatcag agacagaatg cttaacattc atctaacaca taccttgcct   1560

ggtgactttg gtttggttga caaaaatgaa tggcccatga tttgtgcttg gttggtaaag   1620

aatggttacc aatctaccat ggcaagctac tgtgctaaat ggggcaaagt tcctgattgg   1680

tcagaaaact gggcggagcc aaaggtgcca actcctataa atttactagg ttcggcacgc   1740

tcaccattca cgacaccgaa aagtacgcct ctcagccaga actatgcact aactccactt   1800

gcatcggatc tcgaggacct ggctttagag ccttggagca caccaaatac tcctgttgcg   1860

ggcactgcag aaacccagaa cactggggaa gctggttcca aagcctgcca agatggtcaa   1920

ctgagcccaa cttggtcaga gatcgaggag gatttgagag cgtgcttcgg tgcggaaccg   1980

ttgaagaaag acttcagcga gccgctgaac ttggactaa                          2019
```

<210> SEQ ID NO 9
<211> LENGTH: 20
<212> TYPE: PRT
<213> ORGANISM: Part of Parvovirus NS1 Variant

<400> SEQUENCE: 9

```
Thr Arg Ala Cys Arg Ile Phe Ala Phe His Gly Trp Asn Tyr Val Lys
1               5                   10                  15

Val Cys His Ala
            20
```

<210> SEQ ID NO 10
<211> LENGTH: 672
<212> TYPE: PRT
<213> ORGANISM: Parvovirus NS1 Variant

<400> SEQUENCE: 10

```
Met Ala Gly Asn Ala Tyr Ser Asp Glu Val Leu Gly Ala Thr Asn Trp
1               5                   10                  15

Leu Lys Glu Lys Ser Asn Gln Glu Val Phe Ser Phe Val Phe Lys Asn
            20                  25                  30

Glu Asn Val Gln Leu Asn Gly Lys Asp Ile Gly Trp Asn Ser Tyr Lys
        35                  40                  45
```

-continued

```
Lys Glu Leu Gln Glu Asp Glu Leu Lys Ser Leu Gln Arg Gly Ala Glu
    50                  55                  60

Thr Thr Trp Asp Gln Ser Glu Asp Met Glu Trp Glu Thr Thr Val Asp
65                  70                  75                  80

Glu Met Thr Lys Lys Gln Val Phe Ile Phe Asp Ser Leu Val Lys Lys
                85                  90                  95

Cys Leu Phe Glu Val Leu Asn Thr Lys Asn Ile Phe Pro Gly Asp Val
            100                 105                 110

Asn Trp Phe Val Gln His Glu Trp Gly Lys Asp Gln Gly Trp His Cys
        115                 120                 125

His Val Leu Ile Gly Gly Lys Asp Phe Ser Gln Ala Gln Gly Lys Trp
    130                 135                 140

Trp Arg Arg Gln Leu Asn Val Tyr Trp Ser Arg Trp Leu Val Thr Ala
145                 150                 155                 160

Cys Asn Val Gln Leu Thr Pro Ala Glu Arg Ile Lys Leu Arg Glu Ile
                165                 170                 175

Ala Glu Asp Asn Glu Trp Val Thr Leu Leu Thr Tyr Lys His Lys Gln
            180                 185                 190

Thr Lys Lys Asp Tyr Thr Lys Cys Val Leu Phe Gly Asn Met Ile Ala
        195                 200                 205

Tyr Tyr Phe Leu Thr Lys Lys Lys Ile Ser Thr Ser Pro Pro Arg Asp
    210                 215                 220

Gly Gly Tyr Phe Leu Ser Ser Asp Ser Gly Trp Lys Thr Asn Phe Leu
225                 230                 235                 240

Lys Glu Gly Glu Arg His Leu Val Ser Lys Leu Tyr Thr Asp Asp Met
                245                 250                 255

Arg Pro Glu Thr Val Glu Thr Thr Val Thr Thr Ala Gln Glu Thr Lys
            260                 265                 270

Arg Gly Arg Ile Gln Thr Lys Lys Glu Val Ser Ile Lys Thr Thr Leu
        275                 280                 285

Lys Glu Leu Val His Lys Arg Val Thr Ser Pro Glu Asp Trp Met Met
    290                 295                 300

Met Gln Pro Asp Ser Tyr Ile Glu Met Met Ala Gln Pro Gly Gly Glu
305                 310                 315                 320

Asn Leu Leu Lys Asn Thr Leu Glu Ile Cys Thr Leu Thr Leu Ala Arg
                325                 330                 335

Thr Lys Thr Ala Phe Asp Leu Ile Leu Glu Lys Ala Glu Thr Ser Lys
            340                 345                 350

Leu Thr Asn Phe Ser Leu Pro Asp Thr Arg Ala Cys Arg Ile Phe Ala
        355                 360                 365

Phe His Gly Trp Asn Tyr Val Lys Val Cys His Ala Ile Cys Cys Val
    370                 375                 380

Leu Asn Arg Gln Gly Gly Lys Arg Asn Thr Val Leu Phe His Gly Pro
385                 390                 395                 400

Ala Ser Thr Gly Lys Ser Ile Ile Ala Gln Ala Ile Ala Gln Ala Val
                405                 410                 415

Gly Asn Val Gly Cys Tyr Asn Ala Ala Asn Val Asn Phe Pro Phe Asn
            420                 425                 430

Asp Cys Thr Asn Lys Asn Leu Ile Trp Val Glu Glu Ala Gly Asn Phe
        435                 440                 445

Gly Gln Gln Val Asn Gln Phe Lys Ala Ile Cys Ser Gly Gln Thr Ile
    450                 455                 460

Arg Ile Asp Gln Lys Gly Lys Gly Ser Lys Gln Ile Glu Pro Thr Pro
```

-continued 465 470 475 480

Val Ile Met Thr Thr Asn Glu Asn Ile Thr Val Val Arg Ile Gly Cys
485 490 495

Glu Glu Arg Pro Glu His Thr Gln Pro Ile Arg Asp Arg Met Leu Asn
500 505 510

Ile His Leu Thr His His Leu Pro Gly Asp Phe Gly Leu Val Asp Lys
515 520 525

Asn Glu Trp Pro Met Ile Cys Ala Trp Leu Val Lys Asn Gly Tyr Gln
530 535 540

Ser Thr Met Ala Ser Tyr Cys Ala Lys Trp Gly Lys Val Pro Asp Trp
545 550 555 560

Ser Glu Asn Trp Ala Glu Pro Lys Val Pro Thr Pro Ile Asn Leu Leu
565 570 575

Gly Ser Ala Arg Ser Pro Phe Thr Thr Pro Lys Ser Thr Pro Leu Ser
580 585 590

Gln Asn Tyr Ala Leu Thr Pro Leu Ala Ser Asp Leu Glu Asp Leu Ala
595 600 605

Leu Glu Pro Trp Ser Thr Pro Asn Thr Pro Val Ala Gly Thr Ala Glu
610 615 620

Thr Gln Asn Thr Gly Glu Ala Gly Ser Lys Ala Cys Gln Asp Gly Gln
625 630 635 640

Leu Ser Pro Thr Trp Ser Glu Ile Glu Glu Asp Leu Arg Ala Cys Phe
645 650 655

Gly Ala Glu Pro Leu Lys Lys Asp Phe Ser Glu Pro Leu Asn Leu Asp
660 665 670

<210> SEQ ID NO 11
<211> LENGTH: 60
<212> TYPE: DNA
<213> ORGANISM: Part of Parvovirus NS1 Variant

<400> SEQUENCE: 11
atttgctgtg ttttaaacag acaaggaggc aaaagaaatg ctgttttatt tcatggacca 60

<210> SEQ ID NO 12
<211> LENGTH: 2019
<212> TYPE: DNA
<213> ORGANISM: Parvovirus NS1 Variant

<400> SEQUENCE: 12
atggctggaa atgcttactc tgatgaagtt ttgggagcaa ccaactggtt aaaggaaaaa 60
agtaaccagg aagtgttctc atttgttttt aaaaatgaaa atgttcaact gaatggaaaa 120
gatatcggat ggaatagtta caaaaaagag ctgcaggagg acgagctgaa atctttacaa 180
cgaggagcgg aaactacttg ggaccaaagc gaggacatgg aatgggaaac cacagtggat 240
gaaatgacca aaaagcaagt attcattttt gattctttgg ttaaaaaatg tttatttgaa 300
gtgcttaaca caaagaatat atttcctggt gatgttaatt ggtttgtgca acatgaatgg 360
ggaaaagacc aaggctggca ctgccatgta ctaattggag gaaaggactt tagtcaagct 420
caagggaaat ggtggagaag gcaactaaat gtttactgga gcagatggtt ggtaacagcc 480
tgtaatgtgc aactaacacc agctgaaaga attaaactaa gagaaatagc agaagacaat 540
gagtgggtta ctctacttac ttataagcat aagcaaacca aaaaagacta taccaagtgt 600
gttctttttg gaaacatgat tgcttactat tttttaacta aaaagaaaat aagcactagt 660
ccaccaagag acggaggcta ttttcttagc agtgactctg gctggaaaac taacttttta 720
aaagaaggcg agcgccatct agtgagcaaa ctatacactg atgacatgcg gccagaaacg 780
gttgaaacca cagtaaccac tgcgcaggaa actaagcgcg gcagaattca aactaaaaaa 840
gaagtttcta ttaaaactac acttaaagag ctggtgcata aaagagtaac ctcaccagag 900
gactggatga tgatgcagcc agacagttac attgaaatga tggctcaacc aggtggagaa 960
aacctgctga aaaatacgct agagatttgt acactaactc tagccagaac caaaacagca 1020
tttgacttaa ttttagaaaa agctgaaacc agcaaactaa ccaactttc actgcctgac 1080
acaagaacct gcagaatttt tgcttttcat ggctggaact atgttaaagt ttgccatgct 1140
atttgctgtg ttttaaacag acaaggaggc aaaagaaatg ctgttttatt tcatggacca 1200
gccagcacag gcaaatctat tattgcacaa gccatagcac aagcagttgg caatgttggt 1260
tgctataatg cagccaatgt aaactttcca tttaatgact gtaccaacaa gaacttgatt 1320
tgggtagaag aagctggtaa ctttggacag caagtaaacc agtttaaagc catttgctct 1380

-continued

```
ggtcaaacta ttcgcattga tcaaaaagga aaaggcagca aacagattga accaacacca   1440
gtcatcatga ccacaaatga gaacattaca gtggtcagaa taggctgcga agaaagacca   1500
gaacacactc aaccaatcag agacagaatg cttaacattc atctaacaca taccttgcct   1560
ggtgactttg gtttggttga caaaaatgaa tggcccatga tttgtgcttg gttggtaaag   1620
aatggttacc aatctaccat ggcaagctac tgtgctaaat ggggcaaagt tcctgattgg   1680
tcagaaaact gggcggagcc aaaggtgcca actcctataa atttactagg ttcggcacgc   1740
tcaccattca cgacaccgaa aagtacgcct ctcagccaga actatgcact aactccactt   1800
gcatcggatc tcgaggacct ggctttagag ccttggagca caccaaatac tcctgttgcg   1860
ggcactgcag aaacccagaa cactggggaa gctggttcca aagcctgcca agatggtcaa   1920
ctgagcccaa cttggtcaga gatcgaggag gatttgagag cgtgcttcgg tgcggaaccg   1980
ttgaagaaag acttcagcga gccgctgaac ttggactaa                          2019
```

SEQ ID NO 13
LENGTH: 20
TYPE: PRT
ORGANISM: Part of Parvovirus NS1 Variant

SEQUENCE: 13

```
Ile Cys Cys Val Leu Asn Arg Gln Gly Gly Lys Arg Asn Ala Val Leu
1               5                   10                  15

Phe His Gly Pro
            20
```

<210> SEQ ID NO 14
<211> LENGTH: 672
<212> TYPE: PRT
<213> ORGANISM: Parvovirus NS1 Variant

<400> SEQUENCE: 14

```
Met Ala Gly Asn Ala Tyr Ser Asp Glu Val Leu Gly Ala Thr Asn Trp
1               5                   10                  15

Leu Lys Glu Lys Ser Asn Gln Glu Val Phe Ser Phe Val Phe Lys Asn
            20                  25                  30

Glu Asn Val Gln Leu Asn Gly Lys Asp Ile Gly Trp Asn Ser Tyr Lys
        35                  40                  45

Lys Glu Leu Gln Glu Asp Glu Leu Lys Ser Leu Gln Arg Gly Ala Glu
    50                  55                  60

Thr Thr Trp Asp Gln Ser Glu Asp Met Glu Trp Glu Thr Thr Val Asp
65                  70                  75                  80

Glu Met Thr Lys Lys Gln Val Phe Ile Phe Asp Ser Leu Val Lys Lys
                85                  90                  95

Cys Leu Phe Glu Val Leu Asn Thr Lys Asn Ile Phe Pro Gly Asp Val
            100                 105                 110

Asn Trp Phe Val Gln His Glu Trp Gly Lys Asp Gln Gly Trp His Cys
        115                 120                 125

His Val Leu Ile Gly Gly Lys Asp Phe Ser Gln Ala Gln Gly Lys Trp
    130                 135                 140

Trp Arg Arg Gln Leu Asn Val Tyr Trp Ser Arg Trp Leu Val Thr Ala
145                 150                 155                 160

Cys Asn Val Gln Leu Thr Pro Ala Glu Arg Ile Lys Leu Arg Glu Ile
                165                 170                 175

Ala Glu Asp Asn Glu Trp Val Thr Leu Leu Thr Tyr Lys His Lys Gln
            180                 185                 190

Thr Lys Lys Asp Tyr Thr Lys Cys Val Leu Phe Gly Asn Met Ile Ala
        195                 200                 205

Tyr Tyr Phe Leu Thr Lys Lys Lys Ile Ser Thr Ser Pro Pro Arg Asp
    210                 215                 220

Gly Gly Tyr Phe Leu Ser Ser Asp Ser Gly Trp Lys Thr Asn Phe Leu
225                 230                 235                 240
```

-continued

```
Lys Glu Gly Glu Arg His Leu Val Ser Lys Leu Tyr Thr Asp Asp Met
                245                 250                 255

Arg Pro Glu Thr Val Glu Thr Thr Val Thr Thr Ala Gln Glu Thr Lys
            260                 265                 270

Arg Gly Arg Ile Gln Thr Lys Lys Glu Val Ser Ile Lys Thr Thr Leu
        275                 280                 285

Lys Glu Leu Val His Lys Arg Val Thr Ser Pro Glu Asp Trp Met Met
    290                 295                 300

Met Gln Pro Asp Ser Tyr Ile Glu Met Met Ala Gln Pro Gly Gly Glu
305                 310                 315                 320

Asn Leu Leu Lys Asn Thr Leu Glu Ile Cys Thr Leu Thr Leu Ala Arg
                325                 330                 335

Thr Lys Thr Ala Phe Asp Leu Ile Leu Glu Lys Ala Glu Thr Ser Lys
            340                 345                 350

Leu Thr Asn Phe Ser Leu Pro Asp Thr Arg Thr Cys Arg Ile Phe Ala
        355                 360                 365

Phe His Gly Trp Asn Tyr Val Lys Val Cys His Ala Ile Cys Cys Val
    370                 375                 380

Leu Asn Arg Gln Gly Gly Lys Arg Asn Ala Val Leu Phe His Gly Pro
385                 390                 395                 400

Ala Ser Thr Gly Lys Ser Ile Ile Ala Gln Ala Ile Ala Gln Ala Val
                405                 410                 415

Gly Asn Val Gly Cys Tyr Asn Ala Ala Asn Val Asn Phe Pro Phe Asn
            420                 425                 430

Asp Cys Thr Asn Lys Asn Leu Ile Trp Val Glu Glu Ala Gly Asn Phe
        435                 440                 445

Gly Gln Gln Val Asn Gln Phe Lys Ala Ile Cys Ser Gly Gln Thr Ile
    450                 455                 460

Arg Ile Asp Gln Lys Gly Lys Gly Ser Lys Gln Ile Glu Pro Thr Pro
465                 470                 475                 480

Val Ile Met Thr Thr Asn Glu Asn Ile Thr Val Val Arg Ile Gly Cys
                485                 490                 495

Glu Glu Arg Pro Glu His Thr Gln Pro Ile Arg Asp Arg Met Leu Asn
            500                 505                 510

Ile His Leu Thr His His Leu Pro Gly Asp Phe Gly Leu Val Asp Lys
        515                 520                 525

Asn Glu Trp Pro Met Ile Cys Ala Trp Leu Val Lys Asn Gly Tyr Gln
    530                 535                 540

Ser Thr Met Ala Ser Tyr Cys Ala Lys Trp Gly Lys Val Pro Asp Trp
545                 550                 555                 560

Ser Glu Asn Trp Ala Glu Pro Lys Val Pro Thr Pro Ile Asn Leu Leu
                565                 570                 575

Gly Ser Ala Arg Ser Pro Phe Thr Thr Pro Lys Ser Thr Pro Leu Ser
            580                 585                 590

Gln Asn Tyr Ala Leu Thr Pro Leu Ala Ser Asp Leu Glu Asp Leu Ala
        595                 600                 605

Leu Glu Pro Trp Ser Thr Pro Asn Thr Pro Val Ala Gly Thr Ala Glu
    610                 615                 620

Thr Gln Asn Thr Gly Glu Ala Gly Ser Lys Ala Cys Gln Asp Gly Gln
625                 630                 635                 640

Leu Ser Pro Thr Trp Ser Glu Ile Glu Glu Asp Leu Arg Ala Cys Phe
                645                 650                 655

Gly Ala Glu Pro Leu Lys Lys Asp Phe Ser Glu Pro Leu Asn Leu Asp
```

-continued 660 665 670

<210> SEQ ID NO 15
<211> LENGTH: 60
<212> TYPE: DNA
<213> ORGANISM: Part of Parvovirus NS1 Variant

<400> SEQUENCE: 15
ggtcaagcta ttcgcattga tcaaaaagga aaaggcagca aacagattga accaacacca 60

<210> SEQ ID NO 16
<211> LENGTH: 2019
<212> TYPE: DNA
<213> ORGANISM: Parvovirus NS1 Variant

<400> SEQUENCE: 16
atggctggaa atgcttactc tgatgaagtt ttgggagcaa ccaactggtt aaaggaaaaa 60
agtaaccagg aagtgttctc atttgttttt aaaaatgaaa atgttcaact gaatggaaaa 120
gatatcggat ggaatagtta caaaaaagag ctgcaggagg acgagctgaa atctttacaa 180
cgaggagcgg aaactacttg ggaccaaagc gaggacatgg aatgggaaac cacagtggat 240
gaaatgacca aaaagcaagt attcattttt gattctttgg ttaaaaaatg tttatttgaa 300
gtgcttaaca caaagaatat atttcctggt gatgttaatt ggtttgtgca acatgaatgg 360
ggaaaagacc aaggctggca ctgccatgta ctaattggag gaaaggactt tagtcaagct 420
caagggaaat ggtggagaag gcaactaaat gtttactgga gcagatggtt ggtaacagcc 480
tgtaatgtgc aactaacacc agctgaaaga attaaactaa gagaaatagc agaagacaat 540
gagtgggtta ctctacttac ttataagcat aagcaaacca aaaaagacta taccaagtgt 600
gttctttttg gaaacatgat tgcttactat tttttaacta aaaagaaaat aagcactagt 660
ccaccaagag acggaggcta ttttcttagc agtgactctg gctggaaaac taacttttta 720
aaagaaggcg agcgccatct agtgagcaaa ctatacactg atgacatgcg gccagaaacg 780
gttgaaacca cagtaaccac tgcgcaggaa actaagcgcg gcagaattca aactaaaaaa 840
gaagtttcta ttaaaactac acttaaagag ctggtgcata aaagagtaac ctcaccagag 900
gactggatga tgatgcagcc agacagttac attgaaatga tggctcaacc aggtggagaa 960
aacctgctga aaaatacgct agagatttgt acactaactc tagccagaac caaaacagca 1020
tttgacttaa ttttagaaaa agctgaaacc agcaaactaa ccaacttttc actgcctgac 1080
acaagaacct gcagaatttt tgcttttcat ggctggaact atgttaaagt ttgccatgct 1140
atttgctgtg ttttaaacag acaaggaggc aaaagaaata ctgttttatt tcatggacca 1200
gccagcacag gcaaatctat tattgcacaa gccatagcac aagcagttgg caatgttggt 1260
tgctataatg cagccaatgt aaactttcca tttaatgact gtaccaacaa gaacttgatt 1320
tgggtagaag aagctggtaa ctttggacag caagtaaacc agtttaaagc catttgctct 1380
ggtcaagcta ttcgcattga tcaaaaagga aaaggcagca aacagattga accaacacca 1440
gtcatcatga ccacaaatga gaacattaca gtggtcagaa taggctgcga agaaagacca 1500
gaacacactc aaccaatcag agacagaatg cttaacattc atctaacaca taccttgcct 1560
ggtgactttg gtttggttga caaaaatgaa tggcccatga tttgtgcttg gttggtaaag 1620
aatggttacc aatctaccat ggcaagctac tgtgctaaat ggggcaaagt tcctgattgg 1680
tcagaaaact gggcggagcc aaaggtgcca actcctataa atttactagg ttcggcacgc 1740
tcaccattca cgacaccgaa aagtacgcct ctcagccaga actatgcact aactccactt 1800

-continued

```
gcatcggatc tcgaggacct ggctttagag ccttggagca caccaaatac tcctgttgcg   1860

ggcactgcag aaacccagaa cactggggaa gctggttcca aagcctgcca agatggtcaa   1920

ctgagcccaa cttggtcaga gatcgaggag gatttgagag cgtgcttcgg tgcggaaccg   1980

ttgaagaaag acttcagcga gccgctgaac ttggactaa                          2019


<210> SEQ ID NO 17
<211> LENGTH: 20
<212> TYPE: PRT
<213> ORGANISM: Part of Parvovirus NS1 Variant

<400> SEQUENCE: 17

Gly Gln Ala Ile Arg Ile Asp Gln Lys Gly Lys Gly Ser Lys Gln Ile
1               5                   10                  15

Glu Pro Thr Pro
            20


<210> SEQ ID NO 18
<211> LENGTH: 672
<212> TYPE: PRT
<213> ORGANISM: Parvovirus NS1 Variant

<400> SEQUENCE: 18

Met Ala Gly Asn Ala Tyr Ser Asp Glu Val Leu Gly Ala Thr Asn Trp
1               5                   10                  15

Leu Lys Glu Lys Ser Asn Gln Glu Val Phe Ser Phe Val Phe Lys Asn
            20                  25                  30

Glu Asn Val Gln Leu Asn Gly Lys Asp Ile Gly Trp Asn Ser Tyr Lys
        35                  40                  45

Lys Glu Leu Gln Glu Asp Glu Leu Lys Ser Leu Gln Arg Gly Ala Glu
    50                  55                  60

Thr Thr Trp Asp Gln Ser Glu Asp Met Glu Trp Glu Thr Thr Val Asp
65                  70                  75                  80

Glu Met Thr Lys Lys Gln Val Phe Ile Phe Asp Ser Leu Val Lys Lys
                85                  90                  95

Cys Leu Phe Glu Val Leu Asn Thr Lys Asn Ile Phe Pro Gly Asp Val
            100                 105                 110

Asn Trp Phe Val Gln His Glu Trp Gly Lys Asp Gln Gly Trp His Cys
        115                 120                 125

His Val Leu Ile Gly Gly Lys Asp Phe Ser Gln Ala Gln Gly Lys Trp
    130                 135                 140

Trp Arg Arg Gln Leu Asn Val Tyr Trp Ser Arg Trp Leu Val Thr Ala
145                 150                 155                 160

Cys Asn Val Gln Leu Thr Pro Ala Glu Arg Ile Lys Leu Arg Glu Ile
                165                 170                 175

Ala Glu Asp Asn Glu Trp Val Thr Leu Leu Thr Tyr Lys His Lys Gln
            180                 185                 190

Thr Lys Lys Asp Tyr Thr Lys Cys Val Leu Phe Gly Asn Met Ile Ala
        195                 200                 205

Tyr Tyr Phe Leu Thr Lys Lys Lys Ile Ser Thr Ser Pro Pro Arg Asp
    210                 215                 220

Gly Gly Tyr Phe Leu Ser Ser Asp Ser Gly Trp Lys Thr Asn Phe Leu
225                 230                 235                 240

Lys Glu Gly Glu Arg His Leu Val Ser Lys Leu Tyr Thr Asp Asp Met
                245                 250                 255
```

-continued

```
Arg Pro Glu Thr Val Glu Thr Thr Val Thr Thr Ala Gln Glu Thr Lys
            260                 265                 270

Arg Gly Arg Ile Gln Thr Lys Lys Glu Val Ser Ile Lys Thr Thr Leu
        275                 280                 285

Lys Glu Leu Val His Lys Arg Val Thr Ser Pro Glu Asp Trp Met Met
    290                 295                 300

Met Gln Pro Asp Ser Tyr Ile Glu Met Met Ala Gln Pro Gly Gly Glu
305                 310                 315                 320

Asn Leu Leu Lys Asn Thr Leu Glu Ile Cys Thr Leu Thr Leu Ala Arg
                325                 330                 335

Thr Lys Thr Ala Phe Asp Leu Ile Leu Glu Lys Ala Glu Thr Ser Lys
            340                 345                 350

Leu Thr Asn Phe Ser Leu Pro Asp Thr Arg Thr Cys Arg Ile Phe Ala
        355                 360                 365

Phe His Gly Trp Asn Tyr Val Lys Val Cys His Ala Ile Cys Cys Val
    370                 375                 380

Leu Asn Arg Gln Gly Gly Lys Arg Asn Thr Val Leu Phe His Gly Pro
385                 390                 395                 400

Ala Ser Thr Gly Lys Ser Ile Ile Ala Gln Ala Ile Ala Gln Ala Val
                405                 410                 415

Gly Asn Val Gly Cys Tyr Asn Ala Ala Asn Val Asn Phe Pro Phe Asn
            420                 425                 430

Asp Cys Thr Asn Lys Asn Leu Ile Trp Val Glu Glu Ala Gly Asn Phe
        435                 440                 445

Gly Gln Gln Val Asn Gln Phe Lys Ala Ile Cys Ser Gly Gln Ala Ile
    450                 455                 460

Arg Ile Asp Gln Lys Gly Lys Gly Ser Lys Gln Ile Glu Pro Thr Pro
465                 470                 475                 480

Val Ile Met Thr Thr Asn Glu Asn Ile Thr Val Val Arg Ile Gly Cys
                485                 490                 495

Glu Glu Arg Pro Glu His Thr Gln Pro Ile Arg Asp Arg Met Leu Asn
            500                 505                 510

Ile His Leu Thr His His Leu Pro Gly Asp Phe Gly Leu Val Asp Lys
        515                 520                 525

Asn Glu Trp Pro Met Ile Cys Ala Trp Leu Val Lys Asn Gly Tyr Gln
    530                 535                 540

Ser Thr Met Ala Ser Tyr Cys Ala Lys Trp Gly Lys Val Pro Asp Trp
545                 550                 555                 560

Ser Glu Asn Trp Ala Glu Pro Lys Val Pro Thr Pro Ile Asn Leu Leu
                565                 570                 575

Gly Ser Ala Arg Ser Pro Phe Thr Thr Pro Lys Ser Thr Pro Leu Ser
            580                 585                 590

Gln Asn Tyr Ala Leu Thr Pro Leu Ala Ser Asp Leu Glu Asp Leu Ala
        595                 600                 605

Leu Glu Pro Trp Ser Thr Pro Asn Thr Pro Val Ala Gly Thr Ala Glu
    610                 615                 620

Thr Gln Asn Thr Gly Glu Ala Gly Ser Lys Ala Cys Gln Asp Gly Gln
625                 630                 635                 640

Leu Ser Pro Thr Trp Ser Glu Ile Glu Glu Asp Leu Arg Ala Cys Phe
                645                 650                 655

Gly Ala Glu Pro Leu Lys Lys Asp Phe Ser Glu Pro Leu Asn Leu Asp
            660                 665                 670
```

PARVOVIRUS NS1 VARIANTS

CROSS-REFERENCE TO RELATED APPLICATIONS

This application is filed under the provisions of 35 U. S.C. §371 and claims the priority of International Patent Application No. PCT/EP00/07835 filed Aug. 11, 2000, which in turn claims priority of European Patent Application No. 99 115 161.4 filed Aug. 13, 1999.

The present invention relates to parvovirus NS1 variants, DNAs coding for them and methods of producing the parvovirus NS1 variants. Furthermore, this invention concerns antibodies directed against the parvovirus NS1 variants as well as the use of the DNAs and the parvovirus NS1 variants.

Parvovirus designates a genus of the virus family Parvoviridae. The parvovirus genus comprises a number of small, icosaedric viruses that can replicate in the absence of a helper virus. Parvovirus contains a single-stranded DNA having a length of about 5.000 bp. At the 3' and 5' ends of the DNA there is one palindromic sequence each. The DNA codes for two capsid proteins, VP1 and VP2, as well as for two regulatory non-structure proteins, NS-1 and NS-2. The latter proteins are phosphorylated and show nuclear or both cytoplasmic and nuclear localization, respectively. NS1 is necessary for viral DMA replication and participates in the regulation of viral gene expression. Particularly, NS1 transactivates the promoter P38 and exhibits DNA-binding, helicase and DNA-nicking activities. Furthermore, NS1 induces cytotoxic and/or cytostatic stress in sensitive host cells.

Parvoviruses are usually well-tolerated by populations of their natural host, in which they persist without apparent pathological signs. This is due to both the protection of foetuses and neonates by maternal immunity, and the striking restriction of parvovirus replication to a narrow range of target proliferating tissues in adult animals. This host tolerance concerns especially rodent parvoviruses, for example the minute virus of mice (MVM) and H-1 virus in their respective natural hosts, namely mice and rats. In addition, humans can be infected with the latter viruses, without any evidence of associated deleterious effects from existing epidemiological studies and clinical trials. On the other hand, it is known that certain parvoviruses, and especially rodent parvoviruses, are both oncotropic, i.e. accumulate preferentially in neoplastic versus normal tissues, and oncosuppressive, i.e. have a tumor-suppressive effect towards tumor cells, in various animal models. At least part of the oncosuppressive effect is thought to be due to a direct oncolytic action mediated by NS1. This oncosuppressive effect was also demonstrated against human tumor cells transplanted in recipient animals.

It is considered to use parvoviruses for therapeutic purposes. On the one hand, it seems to be of interest to use parvoviruses as vectors for therapeutic genes, i.e. for introducing such genes into the genome of cells. On the other hand, it is considered to use NS1 of parvoviruses as a toxin for treating tumoral diseases. However, initial experiments showed unsatisfactory results.

Therefore, it is the object of the present invention to provide a product by which parvoviruses and NS1 thereof, respectively, can be used for the above purposes.

According to the invention this is achieved by the subject matters defined in the claims.

The present invention Is based on the applicant's findings that it is possible to interfere with the activities of parvovirus NS1 so as to shift the equilibrium existing between the DNA replication and transcription activities (a) and the cytotoxicity activity (b). In particular, he produced parvovirus NS1 variants in which the DNA replication and transcription activities (a) are reduced and eliminated, respectively, whereas the cytotoxicity activity (b) is maintained or raised. Moreover, he produced parvovirus NS1 variants in which the cytotoxicity activity (b) is reduced and eliminated, respectively, whereas the DNA replication and transcription activities (a) are maintained or raised. Examples of such parvovirus NS1 variants are indicated in Table 1 and FIG. 1. In addition, the applicant recognized that the above parvovirus NS1 variants and expression vectors coding for them, particularly parvoviruses, respectively, are suitable for therapeutic purposes.

According to the invention, the applicant's findings are used to provide a parvovirus NS1 variant in which the equilibrium between the DNA replication and transcription activities (a) and the cytotoxicity activity (b) is shifted.

The expression "parvovirus" comprises any parvovirus, particularly a rodent parvovirus, such as minute virus of mice (MVM) and H-1 virus.

The expression "the equilibrium between the DNA replication and transcription activities (a) and the cytotoxicity activity (b) is shifted" refers to the fact that in a parvovirus NS1 variant according to the invention such an equilibrium is shifted as compared to the parvovirus NS1 wild-type. In particular, the equilibrium can be shifted to the effect that the DNA replication and transcription activities (a) are reduced and eliminated, respectively, whereas the cytotoxicity activity (b) is maintained or raised. The cytotoxicity activity (b) can also be reduced and eliminated, respectively, whereas the DNA replication and transcription activities (a) are maintained or raised. Such an equilibrium can be determined by various methods. As regards the determination of the DNA replication activity, reference is made e.g. to methods described in Legendre and Rommelaere, 1992, J. Virol. 66, 5705; Cotmore et al., 1992, Virology 190, 365; Cotmore et al., 1993, J. virol. 67, 1579, Cotmore and Tattersall, 1994, Embo. J. 13, 4145. As to the determination of the transcription activity reference is made to methods described e.g. in Rhode and Richards, 1987, J. Virol. 61, 2807. Regarding the determination of the cytotoxicity activity reference is made to the below examples.

According to the invention parvovirus NS1 variants are preferred in which the shift of equilibrium is achieved by mutation of one or several phosphorylation sites. Particularly preferred are parvovirus NS1 variants that have a mutation at one or several of the phosphorylation sites 283, 363, 394 and 463. Even more preferred are the parvovirus NS1 variants S283A (SEQ ID NO. 6), T363A (SEQ ID NO. 10), T394A (SEQ ID NO. 14) and T463A (SEQ ID NO. 180), which are indicated in Table 1 and FIGS. 1.1, 1.2, 1.3 and 1.4. In S283A, a serine is exchanged by an alanine at position 283, in T363A, a threonine is exchanged by alanine at position 363, in T394A a threonine is exchanged by alanine at position 394 and in T463A a threonine is exchanged by alanine at position 463.

A further subject matter of the present invention relates to a nucleic acid, particularly a DNA, which codes for an above parvovirus NS1 variant. Such a DNA comprises preferably:

(a) the DNA of FIG. 1.1 (SEQ ID NO. 4), 1.2 (SEQ ID NO. 8), 1.3 (SEQ ID NO. 12) and 1.4 (SEQ ID NO. 16), respectively (b) a DNA hybridizing with the DNA from (a), said DNA comprising the mutated phosphorylation site of the DNA from (a), or (c) a DNA related to the DNA from (a) or (b) via the degenerated genetic code.

The DNA of (a) was deposited with DSMZ (Deutsche Sammlung von ikroorganismen and Zellkulturen) on Aug. 11, 1999, i.e. FIG. 1.1 as *Escherichia coli* pRSV-NS: S283A under DSM 12994 (SEQ ID NO. 4), FIG. 1.2 as *Escherichia coli* pRSV-NS: T363A under DSM 12995 (SEQ ID NO. 8), FIG. 1.3 as *Escherichia coli* pRSV-NS: T394A under DSM 12996 (SEQ ID NO: 12) and FIG. 1.4 as *Escherichia coli* pRSV-NS: T463A under DSM 12997 (SEQ ID NO. 16).

The expression “hybridizing DNA” refers to a DNA which hybridizes with a DNA from (a) under normal conditions, particularly at 20(C below the melting point of the DNA. In this connection, the expression “hybridizing” refers to conventional hybridization conditions, preferably to hybridization conditions where 5×SSPE, 1 % SDS, 1×Denhardt’s solution are used as solution and the hybridization temperatures are between 35(C and 70(C, preferably 65(C. The hybridization is followed by a wash step first carried out with 2×SSC, 1 % SDS and then with 0.2×SSC at temperatures between 35(C and 70(C, preferably at 65(C. Furthermore, reference is made to Sambrook et al., Molecular Cloning: A Laboratory Manual, 2nd edition, Cold Spring Harbor Laboratory Press, cold Spring Harbor N.Y. (1989).

A DNA according to the invention can be present in a vector and expression vector, respectively. A person skilled in the art is familiar with examples thereof. In the case of an expression vector for *E. coli* these are e.g. pGEMEX, pUC derivatives, pGEX-2T, pET3b, T7 based expression vectors and pQE-8. For the expression in yeast, e.g. pY100 and Ycpad1 have to be mentioned while e.g. pKCR, pEFBOS, cDM8, PMSCND, and pCEV4 have to be indicated for the expression in animal cells. The baculovirus expression vector pAcSGHisNT-A is especially suitable for the expression in insect cells.

In a preferred embodiment, the vector containing the DNA according to the invention is a virus, e.g. an adenovirus, *vaccinia* virus, an AAV virus or a parvovirus, such as MVM or H-1, a parvovirus being preferred. The vector may also be a retrovirus, such as MoMULV, MoKuLV, HaMuSV, NUMTV, RSV or GaLV.

For constructing expression vectors which contain the DNA according to the invention, it is possible to use general methods known in the art. These methods include e.g. in vitro recombination techniques, synthetic methods and in vivo recombination methods as described in Sambrook et al., supra, for example.

Furthermore, the present invention relates to host cells which contain the above described vectors. These host cells include bacteria, yeast, insect and animal cells, preferably mammalian cells. The *E. coli* strains H101, DH1, x1776, JM101, JM109, BL21, XL1Blue and SG 13009, the yeast strain *Saccharomyces cerevisiae* and the animal cells L, A9, 3T3, FM3A, CHO, COS, Vero, HeLa and the insect cells sf9 are preferred. Methods of transforming these host cells, of phenotypically selecting transformants and of expressing the DNA according to the invention by using the above described vectors are known in the art.

Moreover, the present invention relates to antibodies which specifically recognize an above describe parvovirus NS1 variant, i.e. the region of the parvovirus NS1 variant where the mutation responsible for the shifted equilibrium, particularly a mutated phosphorylation site, is located. The antibodies can be monoclonal, polyclonal or synthetic antibodies or fragments thereof, e.g. Fab, Fv or scFV fragments. Preferably monoclonal antibodies are concerned. For the production it is favorable to immunize animals—particularly rabbits or chickens for a polyclonal antibody and mice for a monoclonal antibody—with an above parvovirus NS1 variant or with fragments thereof. Further boosters of the animals can be effected with the same parvovirus NS1 variant or with fragments thereof. The polyclonal antibody can then be obtained from the animal serum and egg yolk, respectively. The monoclonal antibody can be obtained according to standard methods, reference being made particularly to the method by K÷hler and Milstein (Nature 256 (1975), 495) and GalfrÚ (Meth. Enzymol, 73 (1981), 3). In this case, mouse myeloma cells are fused with spleen cells originating from the immunized animals. Antibodies according to the invention can be used in many ways, e.g. for the immunoprecipitation of the above described parvovirus NS1 variants or for the isolation thereof. The antibodies can be bound in immunoassays in liquid phase or to a solid carrier. In this connection, the antibodies can be labeled in various ways. The person skilled in the art is familiar with suitable markers and labeling methods. Examples of immunoassays are ELISA and RIA.

The present invention provides parvovirus NS1 variants in which the equilibrium between the DNA replication and transcription activities (a) and the cytotoxicity activity (b) is shifted. In particular, parvovirus NS1 variants are provided which have a reduced or no cytotoxicity activity, whereas the DNA replication and transcription activities are maintained or increased. Parvovirus NS1 variants are also provided in which the DNA replication and transcription activities are reduced and eliminated, respectively, whereas the cytotoxicity activity is maintained or raised. Thus, the present invention provides products which are suitable for therapeutic purposes. In particular, expression vectors according to the invention, e.g. parvoviruses, can be used for gene-therapeutic measures. Moreover, parvoviruses NS1 variants according to the invention are suitable as toxins, e.g. for treating tumoral diseases.

Therefore, a kit is also provided for the application of the present invention. This kit comprises the following:

(a) a parvovirus NS1 variant according to the invention,
(b) a DNA according to the invention, e.g. an expression vector, particularly a parvovirus,
(c) an antibody according to the invention, as well as
(d) conventional auxiliary agents, such as solvents, buffers, carriers, markers and controls.

Of component (a) to (d) one or more representatives can be present each.

BRIEF DESCRIPTION OF THE DRAWINGS

FIG. 1 shows the DNA and amino acid sequences of parvovirus NS1 variants according to the invention (FIG 1.1 (SEQ ID Nos. 4 and 6 ), 1.2 (SEQ ID Nos. 8 and 10), 1.3 (SEQ ID Nos. 12 and 14) and 1.4 (SEQ ID Nos. 16 and 18)) as compared to parvovirus N1 wild type (SEQ ID Nos. 1 and 2). In this connection, the mutated sites in the parvovirus Ns1 variants according to the invention are labeled each.

The present invention is explained by the examples.

EXAMPLE 1

Preparation and Purification of NS1 Variants According to the Invention

The DNA of the NS1 variant S283A according to the invention was provided as an EcoRV to BstEII fragment obtained by chimeric PCR using two mutagenic primers. This fragment was then inserted into the corresponding cleaved expression vector pTHisNS1 (Nuesch et al., Virology 209, (1995), 122) to obtain pTHis NS1:S283A. Such a vector codes for a fusion protein comprising 6 histidine residues (N terminus partner) and S283A of FIG. 1 (C terminus partner). For expression and purification of S283A the NS1 gene under control of the bacteriophage T7 promoter was transferred into vaccinia virus and expressed in eucaryotic cells by double infection together with vTF7-3 (a vaccinia virus expressing the bacteriophage T7 DNA polymerase). 18 hrs post infection cells were harvested and nuclear extracts prepared. The histidine tagged S283A was then purified by affinity chromatography on Ni-NTA agarose and analyzed by 10% SDS-PAGE (Nuesch et al., supra).

It showed that a parvovirus NS1 variant according to the invention can be prepared in highly pure form.

The NS1 variants T363A, T394A, and T463A were also produced and purified in the same way.

EXAMPLE 2

Preparation and Detection of an Antibody According to the Invention

Tubes were coated with purified NS1 variants prepared as in example 1 and monoclonal antibodies (e.g. scFv) specifically binding to S283A were isolated from human synthetic VH+VL scFV phage library (Griffith et al., EMBO J., 13, (1994), 3245) according to standard panning protocols after >5 isolation and amplification procedures. The variable region of the isolated scFv harbored in the phagemid were sequenced to identify NS1 variant interacting partner proteins harboring such binding motifs from comparison with known genes in the gene bank.

It showed that monoclonal antibodies according to the invention can be isolated.

In addition, the NS1 variants were used for immunization of animals in order to obtain poly- or monoclonal antibodies.

EXAMPLE 3

Characterization of the Parvovirus NS1 Variants S283A, T363A, T394A and T463A According to the Invention The characterization of the parvovirus NS1 variants comprised the determination of the DNA replication, transcription, cytotoxicity, DNA binding, nicking and helicase activities. Known methods were used for this purpose (cf. description, supra). As regards the determination of the helicase activity reference is made to Stahl et al. 1986, EMBO J. 5, 1999. As to the determination of the nicking activity reference is made to Christensen et al., 1997, J. Virol. 71, 1405 and Nuesch et al,, 1995, supra. Regarding the determination of the DNA binding reference is made to Cotmore et al. 1995, J. Virol. 69, 1652. As far as the determination of the cytotoxicity activity is concerned, the following steps were carried out:

NS1 variants were transferred into an expression vector containing the NS1 gene under the control of the parvovirus MVNP4 promoter (genuine promoter driving the non-structural genes of MVM), and the green fluorescent protein (EGFP) under control of an additional promoter. These constructs were then transfected into A9 cells using lipofectamine (GibcoBRL) according to the manufacturer's instruction and the impact of the NS1 variant on the viability of the cells tested in time course experiments. Transfected cells were identified by fluorescence of the EGFP. Toxic effects were determined in comparison to wild type NS1 or a vector containing no NS1 gene as a function of time as well as a measure of cytopathic changes on the cell morphology.

The data indicated in Table 1 were obtained:

TABLE 1

| | S283A | T363A | T394A | T463A | wt |
|---|---|---|---|---|---|
| P38-TA | + | – | – | ++++ | ++++ |
| ACCA | + | ++++ | ++ | ++ | ++ |
| Nick-1 | + | – | – | +++ | +++ |
| Nick-2 | +++ | – | – | ++++ | ++++ |
| Nick-3 | ++ | – | – | | ++++ |
| Heli | ++ | – | (+) | ++++ | ++++ |
| Rep | + | – | – | + | ++++ |
| Cyto | ++++++ | ++ | +++ | (+) | +++ |

EXAMPLE 4

NS1 Variants' Expression After Transduction Using Recombinant Viral Vectors

NS1 expression cassettes containing the NS1 variants according to the invention under control of the parvoviral P4 promoter and a 3' untranslated region from parvovirus MVM to ensure stability and translation of the gene product, were transferred either in a parvovirus genome background as exemplified in example 3, or a heterologous viral genome background, such as vaccinia virus (example 1) or adenovirus. Promoter and terminator regions were exchanged according to the requirements. The nucleic acids containing the NS1 variants were then packaged either in vivo (after transient transfection into eucaryotic cells) or in vitro and the packaged transducing particles were isolated. These transducing units containing NS1 variants were used either for studies concerning gene regulation in tissue culture or animals, but also as therapeutic agents either alone or in combination with other agents (such as cytokines) in gene and cancer therapy approaches.

What is claimed is:

1. A parvovirus NS1 variant protein having a shifted equilibrium between the DNA replication and transcription activities (a) and the cytotoxicity activity (b), wherein the parvovirus NS1 variant protein comprises a mutated phosphorylation site and wherein the shifted equilibrium is selected from the group consisting of (1) DNA replication activity is reduced, transcription activity is eliminated and cytotoxicity is maintained or increased; and (2) DNA replication activity and transcription activity is maintained or increased and cytotoxicity is reduced or eliminated.

2. A parvovirus NS 1 variant protein having a shifted equilibrium between the DNA replication and transcription activities (a), and the cytotoxicity activity (b), wherein the parvovirus NS 1 variant protein comprises at least one mutation located at an amino acid residue site selected from the group consisting of: 283, 363, 394 and 463 of SEQ ID NO. 2.

3. A parvovirus NS 1 variant protein having a shifted equilibrium between the DNA replication and transcription activities (a) and the cytotoxicity activity (b), wherein the parvovirus NS 1 variant comprises a mutation S283A; T363A; T394A or T463A.

4. the parvovirus NS1 variant protein according to claim 3, wherein the protein comprises SEQ ID NO:6, SEQ ID NO: 10, SEQ ID NO: 14, or SEQ ID NO: 18.

5. A DNA, coding for the parvovirus NS1 variant protein according to claim 3.

6. The DNA according to claim 5, wherein the DNA comprises a member selected from the group consisting of (a) the DNA of SEQ ID Nos 4, 8, 12 and 16, said DNA comprising a mutated phosphorylation site, (b) a DNA hybridizing with the DNA from (a) under high stringency conditions, said DNA comprising the mutated phosphorylation site of the DNA from (a), or (c) a DNA related to the DNA from (a) or (b) via the degenerated genetic code.

7. The DNA according to claim 5, wherein the DNA comprises a member selected from the group consisting of the DNA of SEQ ID Nos: 4, 8, 12 and 16.

8. An expression vector, comprising the DNA according to claim 7.

9. An isolated host cell, containing the expression vector according to claim 8.

10. A method of producing the parvovirus NS 1 variant protein according to claim 3, comprising:

(a) transfecting a host cell with a polynucleotide including SEO ID Nos. 4, 8, 12, or 16;

(b) culturing the host cell under conditions sufficient for expression of the narvovirus NS 1 variant protein; and (c) recovering the parvovirus NS 1 variant protein.

11. A Kit comprising at least one member selected from the group consisting of:

(a) a parvovirus NS 1 variant protein comprising a mutation S283A; T363A; T394A or T463A, and (b) a DNA of SEO ID Nos. 4, 8, 12 or 16, and conventional auxiliary agents, comprising solvents, buffers, carriers markers or controls.

* * * * *